US009925334B2

(12) United States Patent
Stewart et al.

(10) Patent No.: US 9,925,334 B2
(45) Date of Patent: *Mar. 27, 2018

(54) MULTI-STATE ALARM SYSTEM FOR A MEDICAL PUMP

(71) Applicant: Baxter International Inc., Deerfield, IL (US)

(72) Inventors: Janice Stewart, Inverness, IL (US); Randolph Meinzer, Spring Grove, IL (US); Debra K. Bello, Vernon Hills, IL (US); Janet Mullan, Antioch, IL (US); Lai H. Wong, Buffalo Grove, IL (US); Brett Todd, Round Lake, IL (US); Todd Kivlehan, Grayslake, IL (US)

(73) Assignee: BAXTER INTERNATIONAL INC., Deerfield, IL (US)

( * ) Notice: Subject to any disclaimer, the term of this patent is extended or adjusted under 35 U.S.C. 154(b) by 538 days.

This patent is subject to a terminal disclaimer.

(21) Appl. No.: 14/610,035

(22) Filed: Jan. 30, 2015

(65) Prior Publication Data
US 2015/0141921 A1 May 21, 2015

Related U.S. Application Data

(63) Continuation of application No. 10/855,857, filed on May 27, 2004, now Pat. No. 8,961,461.

(51) Int. Cl.
*A61M 37/00* (2006.01)
*A61M 5/168* (2006.01)
(Continued)

(52) U.S. Cl.
CPC ........ *A61M 5/16831* (2013.01); *A61M 5/142* (2013.01); *A61M 5/1684* (2013.01);
(Continued)

(58) Field of Classification Search
CPC ............ A61M 5/16831; A61M 5/1684; A61M 2205/18
See application file for complete search history.

(56) References Cited

U.S. PATENT DOCUMENTS 3,715,058 A   2/1973   Clymans
3,877,428 A   4/1975   Seagle et al.
(Continued)

FOREIGN PATENT DOCUMENTS

CN   1327309 A    12/2001
EP   0567945      11/1993
(Continued)

OTHER PUBLICATIONS

Communication from Lorenz Siedler-Gossel to the EPO dated Mar. B, 2012 regarding Opposition against European Patent EP 2060285 81 (27 pages).
(Continued)

*Primary Examiner* — Laura Bouchelle
(74) *Attorney, Agent, or Firm* — K&L Gates LLP

(57) ABSTRACT

A medical fluid delivery system includes an infusion pump configured to deliver medical fluid to a patient according to at least one treatment parameter, and an alarm feature associated with the infusion pump, the alarm feature including (i) a first alarm signal associated with a first event relating to the at least one treatment parameter, (ii) a second alarm signal associated with a second event relating to the at least one treatment parameter, the second alarm signal discernable from the first alarm signal, and (iii) a snooze element configured to deactivate the first alarm signal after the first event has occurred and to enable the second alarm signal to be activated upon occurrence of the second event.

25 Claims, 7 Drawing Sheets

(51) Int. Cl.
*A61M 5/142* (2006.01)
*A61M 5/14* (2006.01)

(52) U.S. Cl.
CPC ....... *A61M 5/1413* (2013.01); *A61M 2205/18* (2013.01); *A61M 2205/3561* (2013.01)

(56) References Cited

U.S. PATENT DOCUMENTS

| | | |
|---|---|---|
| 3,925,762 A | 12/1975 | Heitlinger et al. |
| 4,028,539 A | 6/1977 | Jacobs |
| 4,079,736 A | 3/1978 | Lundquist |
| 4,180,067 A | 12/1979 | Derlien |
| 4,216,462 A | 8/1980 | McGrath et al. |
| 4,321,461 A | 3/1982 | Walker, Jr. et al. |
| 4,391,598 A | 7/1983 | Thompson |
| 4,431,425 A | 2/1984 | Thompson et al. |
| 4,464,172 A | 8/1984 | Lichtenstein |
| 4,493,709 A | 1/1985 | Beard et al. |
| 4,498,843 A | 2/1985 | Schneider et al. |
| 4,529,401 A | 7/1985 | Leslie et al. |
| 4,553,958 A | 11/1985 | LeCocq et al. |
| 4,616,801 A | 10/1986 | Cewers et al. |
| 4,657,490 A | 4/1987 | Abbott |
| 4,658,375 A | 4/1987 | Onogi et al. |
| 4,696,671 A | 9/1987 | Epstein et al. |
| 4,710,166 A | 12/1987 | Thompson et al. |
| 4,714,462 A | 12/1987 | DiDomenico |
| 4,715,385 A | 12/1987 | Cudahy et al. |
| 4,741,736 A | 5/1988 | Brown |
| 4,776,842 A | 10/1988 | Franetzki et al. |
| 4,778,449 A | 10/1988 | Weber et al. |
| 4,785,799 A | 11/1988 | Schoon et al. |
| 4,810,243 A | 3/1989 | Howson |
| 4,820,273 A | 4/1989 | Reinicke |
| 4,828,545 A | 5/1989 | Epstein et al. |
| 4,838,887 A | 6/1989 | Idriss |
| 4,840,542 A | 6/1989 | Abbott |
| 4,842,584 A | 6/1989 | Pastrone |
| 4,857,048 A | 8/1989 | Simons et al. |
| 4,857,713 A | 8/1989 | Brown |
| 4,865,584 A | 9/1989 | Epstein et al. |
| 4,867,170 A | 9/1989 | Takahasi |
| 4,878,175 A | 10/1989 | Norden-Paul et al. |
| 4,895,161 A | 1/1990 | Cudahy et al. |
| 4,931,050 A | 6/1990 | Idriss |
| 4,943,279 A | 7/1990 | Samiotes et al. |
| 4,978,335 A | 12/1990 | Arthur, III |
| 5,002,055 A | 3/1991 | Merki et al. |
| 5,034,004 A | 7/1991 | Crankshaw |
| 5,049,141 A | 9/1991 | Olive |
| 5,072,383 A | 12/1991 | Brimm et al. |
| 5,077,666 A | 12/1991 | Brimm et al. |
| 5,078,683 A | 1/1992 | Sancoff et al. |
| 5,100,380 A | 3/1992 | Epstein et al. |
| 5,108,367 A | 4/1992 | Epstein et al. |
| 5,108,372 A | 4/1992 | Swenson |
| 5,205,819 A | 4/1993 | Ross et al. |
| 5,207,666 A | 5/1993 | Idriss et al. |
| 5,219,330 A | 6/1993 | Bollish et al. |
| 5,274,551 A | 12/1993 | Corby, Jr. |
| 5,304,126 A | 4/1994 | Epstein et al. |
| 5,314,243 A | 5/1994 | McDonald et al. |
| 5,317,506 A | 5/1994 | Coutre et al. |
| 5,325,478 A | 6/1994 | Shelton et al. |
| 5,368,555 A | 11/1994 | Sussman et al. |
| 5,368,562 A | 11/1994 | Blomquist et al. |
| 5,378,231 A | 1/1995 | Johnson et al. |
| 5,379,333 A | 1/1995 | Toth |
| 5,395,340 A | 3/1995 | Lee |
| 5,400,378 A | 3/1995 | Toth |
| 5,429,602 A | 7/1995 | Hauser |
| 5,445,621 A | 8/1995 | Poli et al. |
| 5,458,123 A | 10/1995 | Unger |
| 5,464,392 A | 11/1995 | Epstein et al. |
| 5,483,957 A | 1/1996 | Janssen et al. |
| 5,486,286 A | 1/1996 | Peterson et al. |
| 5,507,412 A | 4/1996 | Ebert et al. |
| 5,514,088 A | 5/1996 | Zakko |
| 5,522,798 A | 6/1996 | Johnson et al. |
| 5,547,470 A | 8/1996 | Johnson et al. |
| 5,558,638 A | 9/1996 | Evers et al. |
| 5,558,640 A | 9/1996 | Pfeiler et al. |
| 5,564,803 A | 10/1996 | McDonald et al. |
| 5,573,506 A | 11/1996 | Vasko |
| 5,586,868 A | 12/1996 | Lawless et al. |
| 5,591,344 A | 1/1997 | Kenley et al. |
| 5,628,619 A | 5/1997 | Wilson |
| 5,640,953 A | 6/1997 | Bishop et al. |
| 5,643,212 A | 7/1997 | Coutre et al. |
| 5,658,250 A | 8/1997 | Blomquist et al. |
| 5,681,285 A | 10/1997 | Ford et al. |
| 5,685,844 A | 11/1997 | Martila |
| 5,713,856 A | 2/1998 | Eggers et al. |
| 5,718,562 A | 2/1998 | Lawless et al. |
| 5,745,378 A | 4/1998 | Barker et al. |
| 5,752,917 A | 5/1998 | Fuchs |
| 5,772,635 A | 6/1998 | Dastur et al. |
| 5,778,882 A | 7/1998 | Raymond et al. |
| 5,781,442 A | 7/1998 | Engleson et al. |
| 5,782,805 A | 7/1998 | Meinzer et al. |
| 5,791,880 A | 8/1998 | Wilson |
| 5,795,327 A | 8/1998 | Wilson et al. |
| 5,807,321 A | 9/1998 | Stoker et al. |
| 5,810,770 A | 9/1998 | Chin et al. |
| 5,814,015 A | 9/1998 | Gargano et al. |
| 5,816,242 A | 10/1998 | Cewers |
| 5,830,187 A | 11/1998 | Kriesel et al. |
| 5,852,590 A | 12/1998 | De la Huerga |
| 5,871,465 A | 2/1999 | Vasko |
| 5,883,576 A | 3/1999 | De La Huerga |
| 5,897,498 A | 4/1999 | Canfield, II et al. |
| D410,081 S | 5/1999 | Sweeney et al. |
| 5,903,889 A | 5/1999 | De la Huerga et al. |
| 5,935,099 A | 8/1999 | Peterson et al. |
| 5,938,607 A | 8/1999 | Jago et al. |
| 5,941,846 A | 8/1999 | Duffy et al. |
| 5,957,885 A | 9/1999 | Bollish et al. |
| 5,960,085 A | 9/1999 | De la Huerga |
| 6,012,034 A | 1/2000 | Hamparian et al. |
| 6,044,134 A | 3/2000 | De la Huerga |
| 6,045,533 A | 4/2000 | Kriesel et al. |
| 6,077,055 A | 6/2000 | Vilks |
| 6,081,048 A | 6/2000 | Bergmann et al. |
| 6,083,206 A | 7/2000 | Molko |
| 6,095,985 A | 8/2000 | Raymond et al. |
| 6,104,941 A | 8/2000 | Huey et al. |
| 6,108,399 A | 8/2000 | Hernandez-Guerra et al. |
| RE36,871 E | 9/2000 | Epstein et al. |
| 6,117,126 A | 9/2000 | Appelbaum et al. |
| 6,123,686 A | 9/2000 | Olsen et al. |
| 6,129,702 A | 10/2000 | Woias et al. |
| 6,141,402 A | 10/2000 | Toth |
| 6,167,012 A | 12/2000 | Van Den Enden et al. |
| 6,182,076 B1 | 1/2001 | Yu et al. |
| 6,183,417 B1 | 2/2001 | Geheb et al. |
| 6,213,939 B1 | 4/2001 | McEwen |
| 6,216,104 B1 | 4/2001 | Moshfeghi et al. |
| 6,231,560 B1 | 5/2001 | Bui et al. |
| 6,241,704 B1 | 6/2001 | Peterson et al. |
| 6,255,951 B1 | 7/2001 | De La Huerga |
| 6,257,936 B1 | 7/2001 | Strandberg |
| 6,259,654 B1 | 7/2001 | De La Huerga |
| 6,260,021 B1 | 7/2001 | Wong et al. |
| 6,264,614 B1 | 7/2001 | Albert et al. |
| 6,269,340 B1 | 7/2001 | Ford et al. |
| 6,272,505 B1 | 8/2001 | De La Huerga |
| 6,283,944 B1 | 9/2001 | McMullen et al. |
| 6,308,171 B1 | 10/2001 | De La Huerga |
| 6,312,227 B1 | 11/2001 | Davis |
| 6,342,841 B1 | 1/2002 | Sting |
| 6,345,268 B1 | 2/2002 | de la Huerga |
| 6,346,886 B1 | 2/2002 | de la Huerga |
| 6,350,239 B1 | 2/2002 | Ohad et al. |
| 6,356,780 B1 | 3/2002 | Licato et al. |

(56) References Cited

U.S. PATENT DOCUMENTS

| | | |
|---|---|---|
| 6,358,237 B1 | 3/2002 | Paukovits et al. |
| 6,362,591 B1 | 3/2002 | Moberg |
| 6,377,223 B1 | 4/2002 | Clapp et al. |
| 6,401,138 B1 | 6/2002 | Judge et al. |
| 6,405,165 B1 | 6/2002 | Blum et al. |
| 6,408,330 B1 | 6/2002 | DeLaHuerga |
| 6,409,659 B1 | 6/2002 | Warner et al. |
| 6,409,696 B1 | 6/2002 | Toavs et al. |
| 6,416,495 B1 | 7/2002 | Kriesel et al. |
| 6,434,567 B1 | 8/2002 | De La Huerga |
| 6,450,956 B1 | 9/2002 | Rappaport et al. |
| 6,462,953 B2 | 10/2002 | Tong et al. |
| 6,468,242 B1 | 10/2002 | Wilson et al. |
| 6,471,645 B1 | 10/2002 | Warkentin et al. |
| 6,471,675 B1 | 10/2002 | Rogers et al. |
| 6,475,146 B1 | 11/2002 | Frelburger et al. |
| 6,475,148 B1 | 11/2002 | Jackson et al. |
| 6,475,180 B2 | 11/2002 | Peterson et al. |
| 6,497,656 B1 | 12/2002 | Evans et al. |
| 6,497,680 B1 | 12/2002 | Holst et al. |
| 6,504,837 B1 | 1/2003 | Menzel |
| 6,506,155 B2 | 1/2003 | Sluis |
| 6,519,569 B1 | 2/2003 | White et al. |
| 6,520,910 B1 | 2/2003 | Kohls |
| 6,537,214 B1 | 3/2003 | Hood et al. |
| 6,537,244 B2 | 3/2003 | Paukovits et al. |
| 6,539,504 B1 | 3/2003 | Knefel |
| 6,542,902 B2 | 4/2003 | Dulong et al. |
| 6,547,748 B1 | 4/2003 | Shine |
| 6,551,243 B2 | 4/2003 | Bocionek et al. |
| 6,551,276 B1 | 4/2003 | Mann et al. |
| 6,554,791 B1 | 4/2003 | Cartledge et al. |
| 6,554,798 B1 | 4/2003 | Mann et al. |
| 6,562,001 B2 | 5/2003 | Lebel et al. |
| 6,571,128 B2 | 5/2003 | Lebel et al. |
| 6,695,823 B1* | 2/2004 | Lina .................... A61F 13/0203 602/43 |
| 6,808,508 B1 | 10/2004 | Zafirelis et al. |
| 8,961,461 B2* | 2/2015 | Stewart ............. A61M 5/16831 604/131 |
| 2001/0017817 A1 | 8/2001 | De La Huerga |
| 2001/0025156 A1 | 9/2001 | Bui et al. |
| 2001/0028308 A1 | 10/2001 | De La Huerga |
| 2001/0031944 A1 | 10/2001 | Peterson et al. |
| 2001/0037083 A1 | 11/2001 | Hartlaub et al. |
| 2002/0002326 A1 | 1/2002 | Causey, III et al. |
| 2002/0016568 A1 | 2/2002 | Lebel et al. |
| 2002/0019606 A1 | 2/2002 | Lebel et al. |
| 2002/0029776 A1 | 3/2002 | Blomquist |
| 2002/0038392 A1 | 3/2002 | De La Huerga |
| 2002/0058906 A1 | 5/2002 | Lebel et al. |
| 2002/0061255 A1 | 5/2002 | Nguyen et al. |
| 2002/0065454 A1 | 5/2002 | Lebel et al. |
| 2002/0065509 A1 | 5/2002 | Lebel et al. |
| 2002/0065540 A1 | 5/2002 | Lebel et al. |
| 2002/0072733 A1 | 6/2002 | Flaherty |
| 2002/0077852 A1 | 6/2002 | Ford et al. |
| 2002/0077865 A1 | 6/2002 | Sullivan |
| 2002/0087120 A1 | 7/2002 | Rogers et al. |
| 2002/0107476 A1 | 8/2002 | Mann et al. |
| 2002/0116509 A1 | 8/2002 | De La Huerga |
| 2002/0123740 A1 | 9/2002 | Flaherty et al. |
| 2002/0126035 A1 | 9/2002 | Hou |
| 2002/0151875 A1 | 10/2002 | Haller |
| 2002/0156462 A1 | 10/2002 | Stultz |
| 2002/0198513 A1 | 12/2002 | Lebel et al. |
| 2003/0036783 A1 | 2/2003 | Bauhahn et al. |
| 2003/0040722 A1 | 2/2003 | Massengale et al. |
| 2003/0050621 A1 | 3/2003 | Lebel et al. |
| 2003/0055406 A1 | 3/2003 | Lebel et al. |
| 2003/0055570 A1 | 3/2003 | Ribeiro, Jr. |
| 2003/0060753 A1 | 3/2003 | Starkweather et al. |
| 2003/0060765 A1 | 3/2003 | Campbell et al. |
| 2003/0065308 A1 | 4/2003 | Lebel et al. |
| 2003/0065370 A1 | 4/2003 | Lebel et al. |
| 2003/0100864 A1 | 5/2003 | Bendsen et al. |
| 2003/0114836 A1 | 6/2003 | Estes et al. |
| 2003/0125612 A1 | 7/2003 | Fox et al. |
| 2003/0128126 A1 | 7/2003 | Burbank et al. |
| 2003/0135087 A1 | 7/2003 | Hickle et al. |
| 2003/0139701 A1 | 7/2003 | White et al. |
| 2003/0163088 A1 | 8/2003 | Blomquist |
| 2003/0163223 A1 | 8/2003 | Blomquist |
| 2003/0163789 A1 | 8/2003 | Blomquist |
| 2003/0167035 A1 | 9/2003 | Flaherty et al. |
| 2003/0176933 A1 | 9/2003 | Lebel et al. |
| 2003/0181851 A1 | 9/2003 | Mann et al. |
| 2003/0181852 A1 | 9/2003 | Mann et al. |
| 2003/0191431 A1 | 10/2003 | Mann et al. |
| 2004/0078231 A1 | 4/2004 | Wilkes et al. |
| 2004/0172222 A1* | 9/2004 | Simpson ............. G06F 19/3418 702/189 |

FOREIGN PATENT DOCUMENTS

| | | |
|---|---|---|
| EP | 0829266 | 3/1998 |
| EP | 1703839 | 9/2006 |
| JP | 3-140164 | 6/1991 |
| JP | 2003-25176 | 1/2003 |
| JP | 2003-70803 | 3/2003 |
| WO | 9523620 | 9/1995 |
| WO | 9721456 A | 6/1997 |
| WO | 0028127 | 5/2000 |
| WO | WO0028217 | 5/2000 |
| WO | 02066101 | 8/2002 |
| WO | 03022127 | 3/2003 |
| WO | 03058567 | 7/2003 |

OTHER PUBLICATIONS

English Translation of Communication from Lorenz Siedler-Gossel to the EPO dated Mar. B, 2012 regarding Opposition against European Patent EP 2060285 81 (24 pages).

Reply of the patent proprietor to the notice(s) of opposition dated May 10, 2013 relating to EP09075083.7.

Annex to communication—opposition dated Mar. 20, 2015 relating to EP09075083.7.

Letter dated Mar. 11, 2016 from Potter Clarkson on behalf of proprietor and appellant Baxter International Inc. regarding the opposition procedure (no time limit) and accompanying auxiliary requests No. 1-12 relating to EP09075083.7.

Decision revoking the European Patent No. EP-B-2 060 285 dated Jun. 23, 2016 relating to EP09075083.7.

Notice of Appeal dated Jul. 22, 2016 and accompanying letter and claims on behalf of proprietor and appellant Baxter International Inc. relating to EP09075083.7.

Grounds of Appeal, accompanying letter and claim requests on behalf of proprietor and appellant Baxter International Inc. dated Oct. 21, 2016 relating to EP09075083.7.

Communication from Lorenz Seidler Gossel dated Feb. 23, 2017 submitting Reply to Appeal on behalf of Opponents and Respondents Fresenius Deutschland GmbH and Fresenius Medical Care Deutschland GmbH relating to EP09075083.7.

Communication from Maikowski & Ninnemann dated Mar. 3, 2017 submitting Reply to Appeal on behalf of Opponents and Respondents Fresenius Deutschland GmbH and Fresenius Medical Care Deutschland GmbH relating to EP09075083.7.

* cited by examiner

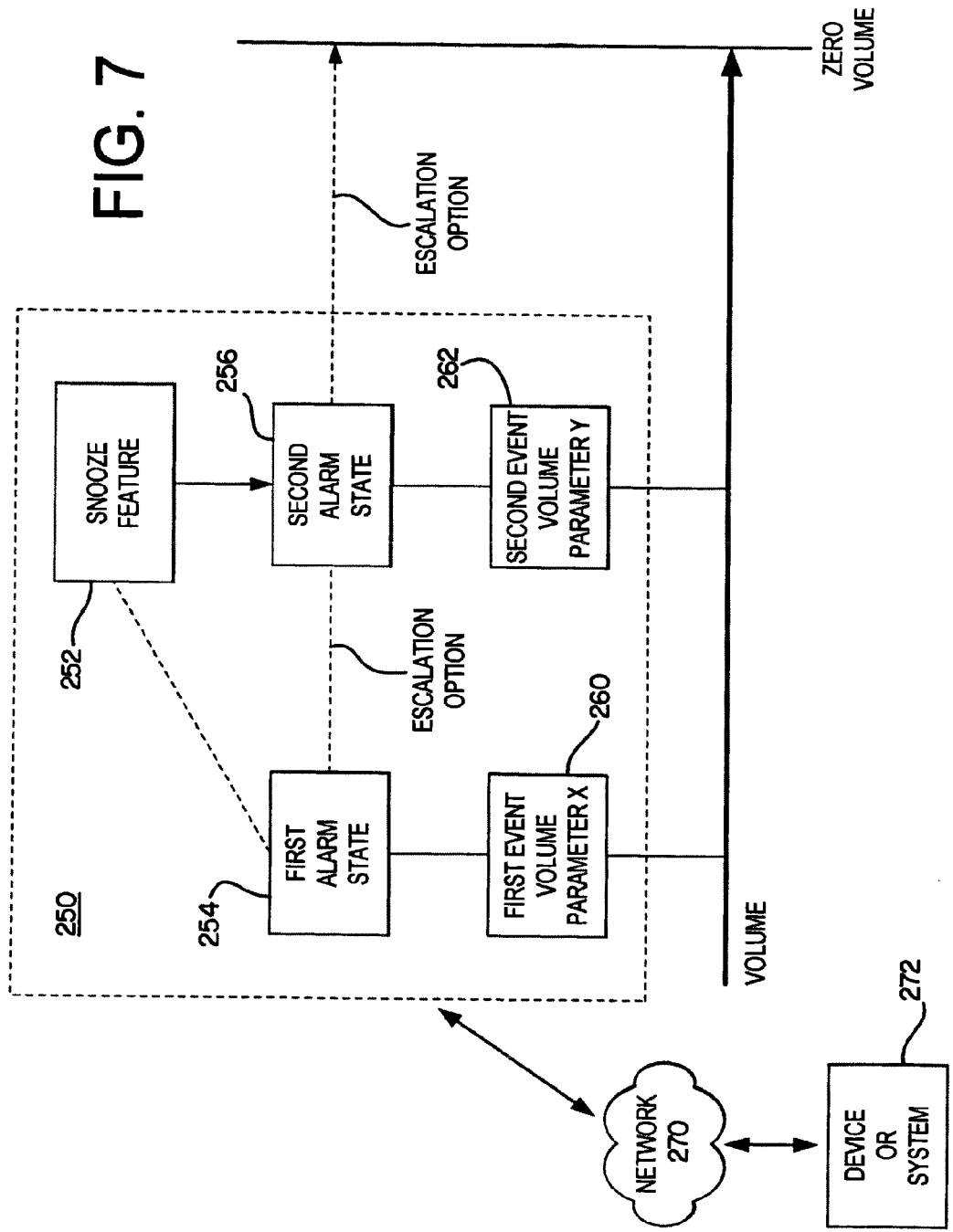

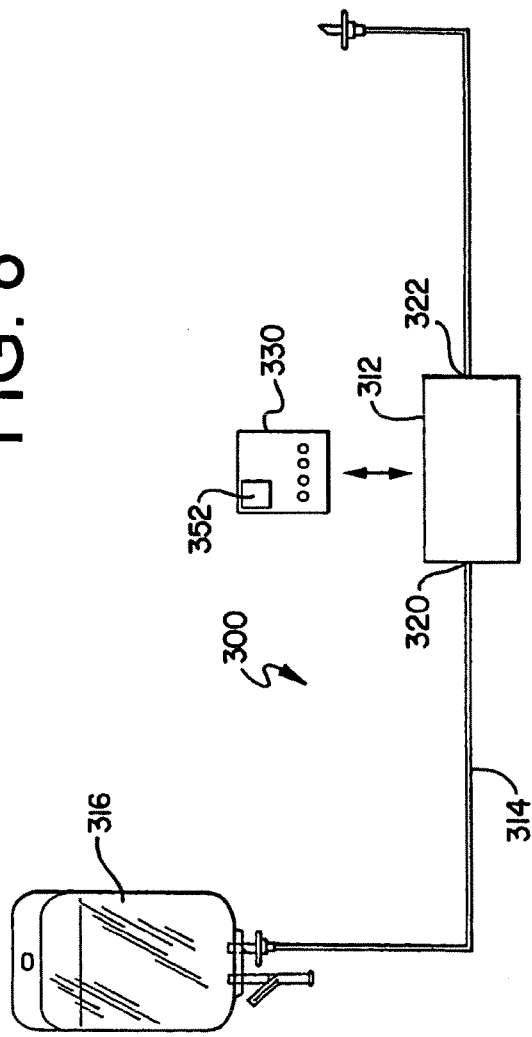

MULTI-STATE ALARM SYSTEM FOR A MEDICAL PUMP

PRIORITY

This application claims priority to and the benefit as a continuation application of U.S. patent application Ser. No. 10/855,857, entitled "Multi-State Alarm System for a Medical Pump", filed May 27, 2004, the entire contents of which is hereby incorporated by reference and relied upon.

TECHNICAL FIELD

The instant invention relates to alarm systems for use with medical delivery pumps for delivery of therapeutic fluids to a patient.

CROSS REFERENCE TO APPLICATIONS

This application expressly incorporates by reference, and makes a part hereof, the following U.S. patent and U.S. patent applications: U.S. Pat. No. 5,782,805; U.S. Pat. No. 5,842,841; U.S. Pat. No. 8,518,021; U.S. patent application Ser. No. 10/855,872; and U.S. Pat. No. 7,927,313.

BACKGROUND OF THE INVENTION

The administration of therapeutic fluids to a patient is well known in the art. Many types of medical delivery devices exist to deliver various therapeutic fluids to a patient, such as, for example, parenteral fluids, drugs or other medicaments, electrolytes, blood and blood products, and the like. One particular type of medical delivery device is an infusion pump, which can deliver one or more of these therapeutic fluids to a patient via a variety of administration types, such as, for example, intravenous (IV), intra-arterial (IA), subcutaneous, epidural, irrigation of fluid spaces applications, and the like. Many infusion pumps that operate under these types of administration typically utilize an administration line set and an associated container containing one or more therapeutic fluids. The line set is typically loaded into a delivery mechanism of the pump, which facilitates delivery of the fluid to the patient.

Each type of administration and each type of therapeutic fluid typically involve numerous operational parameters, variables, constraints and other related information, such as medical and pharmaceutical related information, that must be monitored and followed to ensure proper, effective and safe delivery of therapeutic fluids to the patient and effective treatment of the patient. To ensure proper monitoring and treatment, most medical delivery pumps incorporate an alarm system to indicate to a caregiver or patient that an event has occurred, such as one or more operational parameters being out of a predetermined range. These alarms are typically visual or audible alarms, such as a beeping alarm.

In addition to medical delivery devices, most medical equipment that is utilized in direct patient care typically have alarm systems to notify the caregiver of situations that require attention. While the intent of these alarms is to notify the caregiver of such situations and allow them to be addressed, the shear number of alarm systems of equipment that may be associated with treatment of a particular patient, and the frequency of such alarms being triggered and high levels of patient acuity, have ultimately minimized the sense of urgency in responding to such alarms. This can result in a potentially dangerous situation, particularly in the case of medical pumps utilized to properly and safely deliver fluids, such as drugs, to a patient.

To address this concern, there is a need to distinguish between alarms, and in the case of medical pumps, there is a need to distinguish between alarms associated with the same or separate events that occur in connection with the same or separate devices.

The present invention addresses these and other concerns and generally provides a new and improved alarm system for a medical pump for delivery of medicaments to a patient.

SUMMARY OF THE INVENTION

The present invention generally provides an alarm system for a medical pump associated with delivering a medicament or fluid to a patient in connection with treatment of the patient. According to a particular aspect of the invention, the alarm system comprises an alarm associated with at least one treatment parameter. The alarm includes a first alarm state associated with a first event relating to the at least one treatment parameter and a second alarm state associated with a second event. The second alarm state is discernable from the first alarm state. This will allow each of the events to be treated differently by a caregiver.

According to other aspects of the invention, the alarm may be audible, the alarm may be visual, the alarm may have both audible and visual components, the second alarm state may have a tone that is discernable from the first alarm state, the second alarm state may have a volume level that is discernable from the first alarm state, the second alarm state may have a frequency that is discernable the first alarm state, and/or the second alarm state may have an appearance that is discernable from the first alarm state.

According to another aspect of the invention, the second event relates to the at least one treatment parameter.

According to yet another aspect of the invention, the second event relates to a treatment parameter different from the at least one treatment parameter.

According to yet another aspect of the invention, the second event is defined by expiration of an amount of time measured from occurrence of the first event.

According to yet another aspect of the invention, the second event is defined by a deviation from a value associated with the at least one treatment parameter.

According to yet another aspect of the invention, the at least one treatment parameter is associated with the pump.

According to yet another aspect of the invention, the at least one treatment parameter is associated with a source external to the pump.

According to yet another aspect of the invention, an alarm signal associated with the alarm states is routed to a device external to the pump.

According to a further aspect of the invention, the treatment parameter may be associated with a measurement from the patient, operation of the pump, and/or the fluid.

According to yet another aspect of the invention, the second event may be associated with a life-threatening situation for the patient.

According to yet another aspect of the invention, the pump will shut off when the alarm is in the second alarm state.

According to yet another aspect of the invention, the events can be set by a user.

According to yet another aspect of the invention, the second alarm state will only be operational with a particular fluid. The identification of the particular fluid may be stored in a memory associated with the pump.

According to yet another aspect of the invention, the alarm system can be customizable and include a near-end alert/alarm feature.

According to yet another aspect of the invention, the alarm system can be incorporated into different types of infusion pumps in including a micro electromechanical systems (MEMS) pump.

These and other aspects of the present invention will be apparent from the drawings and written specification set forth herein, including the appended claims.

BRIEF DESCRIPTION OF THE FIGURES

FIG. 7 is a schematic diagram of an example of a particular embodiment and application of the alarm system of the present invention.

FIG. 8 is a schematic diagram of an alternative embodiment of the alarm system of the present invention.

DETAILED DESCRIPTION OF THE PREFERRED EMBODIMENTS

Figure 1:
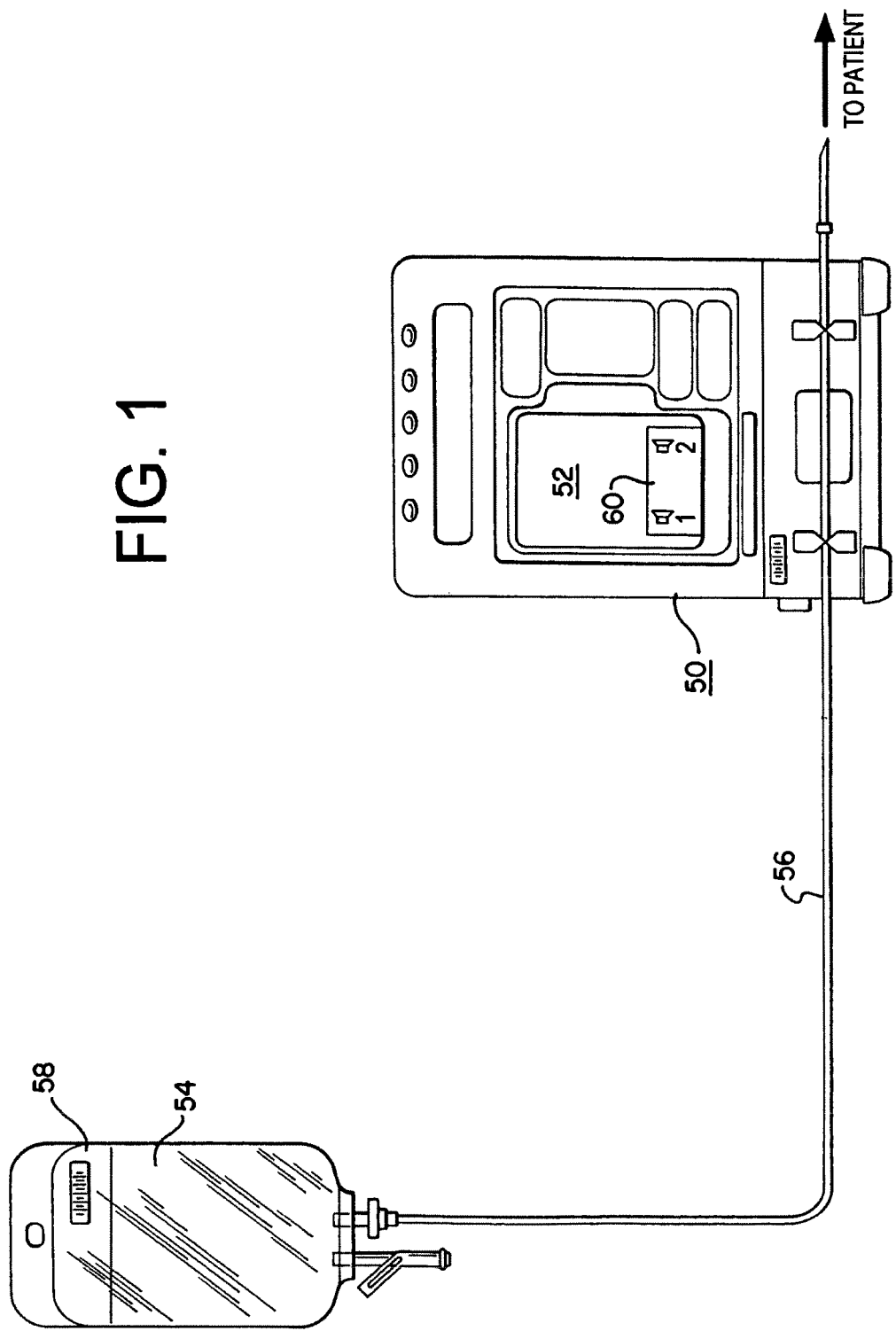
FIG. 1 is a schematic diagram generically depicting an infusion pump having an alarm system in accordance with the principles of the present invention.

While this invention is susceptible to embodiments in many different forms, there are shown in the drawings and herein described in detail, preferred embodiments of the invention with the understanding that the present disclosures are to be considered as exemplifications of the principles of the invention and are not intended to limit the broad aspects of the invention to the embodiments illustrated.

FIG. 1 generically depicts a medical fluid delivery pump 50 having an alarm system 52 in accordance with the principles of the present invention. As is well known in the art, the pump 50 is utilized to deliver a medicament 54, or fluid 54, to a patient via a line set 56 and associated container 58 containing the fluid 54. The pump 50 is preferably a microprocessor-based pump that is capable of being programmed, utilizing software and/or firmware, to facilitate operation and functionality of the pump 50. One preferred embodiment of the pump 50 is the one disclosed in U.S. Pat. Nos. 5,782,805 and 5,842,841, which are incorporated herein by reference.

In a preferred embodiment, the alarm system 52 comprises an alarm 60 having a first alarm state and associated alarm signal (indicated by the speaker icon labeled as "1" in FIG. 1) and a second alarm state and associated alarm signal (indicated by the speaker icon labeled as "2" in FIG. 1). However, any number of alarm states and associated signals could be provided in accordance with the principles of the present invention. The alarm 60 of the alarm system 52 is preferably associated with at least one treatment parameter in connection with treatment of a patient. The treatment parameter may be associated with the pump 50, or it may be associated with an external source that is in communication with the pump alarm system 52. Examples of treatment parameters may include a value representing an infusion rate of a therapeutic fluid being delivered to a patient by a volumetric infusion pump, information relating to operation of the pump, the identification of a drug being delivered to a patient, a measurement taken from a patient by the pump or an external source, or any other information or data associated with the treatment of a patient. As used herein, the term "treatment parameter" is defined to encompass all of the above-described parameters as well as any other types or forms of data, values, parameters, information, units of time, or any discrete measurement or piece of data in connection with treatment of a patient. The alarm 60 is customizable and also can be pre-programmed or set by a caregiver such as at the bedside.

According to a particular aspect of the invention, the first alarm state is preferably associated with a first event relating to a treatment parameter, and the second alarm state is associated with a second event relating to the same or another treatment parameter. The second alarm state is discernable from the first alarm state so that a caregiver can act appropriately to each of the alarm states should they occur during treatment. The alarm 60 can be audible, visual, or a combination thereof. The events may be any number of occurrences relating to the treatment of the patient, such as, for example, measurement of an elapsed time between events, measurement of a value of a treatment parameter, an occurrence relating to operation of the pump, an identification or determination made by the pump or an external device, etc.

In a particular embodiment, the second event can be defined by an amount of time that has expired since the first alarm state has been activated without being addressed by a caregiver. In such a case, the first and second events can be related to the same treatment parameter and the second alarm state is activated only when the particular amount of time has expired since activation of the first alarm state. The second alarm state may be in any form as described herein, such as, for example, an escalation of the frequency or tone of the first alarm state.

In yet another particular embodiment, the second event may be defined by a deviation from a particular value or range of values of a treatment parameter. In such a case, the first and second events can be related to the same treatment parameter. The first event may be defined by a first deviation value or range with respect to an original value of the treatment parameter and the second event may be defined by a second deviation value or range, wherein the second event may be measured with respect to either the original value of the treatment parameter or the first event. The original value may be a predetermined value, either pre-programmed or obtained by an external source. In this particular example, the second alarm state is activated only when a particular value of deviation has occurred with respect to the original value of the treatment parameter or the first event.

In yet another embodiment, the first and second events may be related to different treatment parameters. For example, if the events are each defined by a deviation from a particular value of a treatment parameter, the first and second alarm states would be activated by a deviation of its respective treatment parameters (i.e., first and second events). In such a case, the discernable alarm states would allow a caregiver to identify the particular event associated with the particular alarm state.

Preferably, the second alarm state is associated with an event that is critical, i.e., life-threatening to the patient or of a high level of importance that requires immediate attention, whereas the first alarm state is associated with an event that is non-critical, i.e., non-life-threatening to the patient or of a lower level of importance that does not require immediate attention. However, the alarm states can be customized to be associated with, or categorized by, any type of event or occurrence. The event can be any occurrence related to the treatment parameter, such as, for example, a deviation from the treatment parameter or a flag raised by a treatment protocol that is triggered by the treatment parameter. The events may be associated with administration of a fluid to a patient, a measurement from a patient, the operation of the pump, or any other aspect of treatment.

Figure 2:
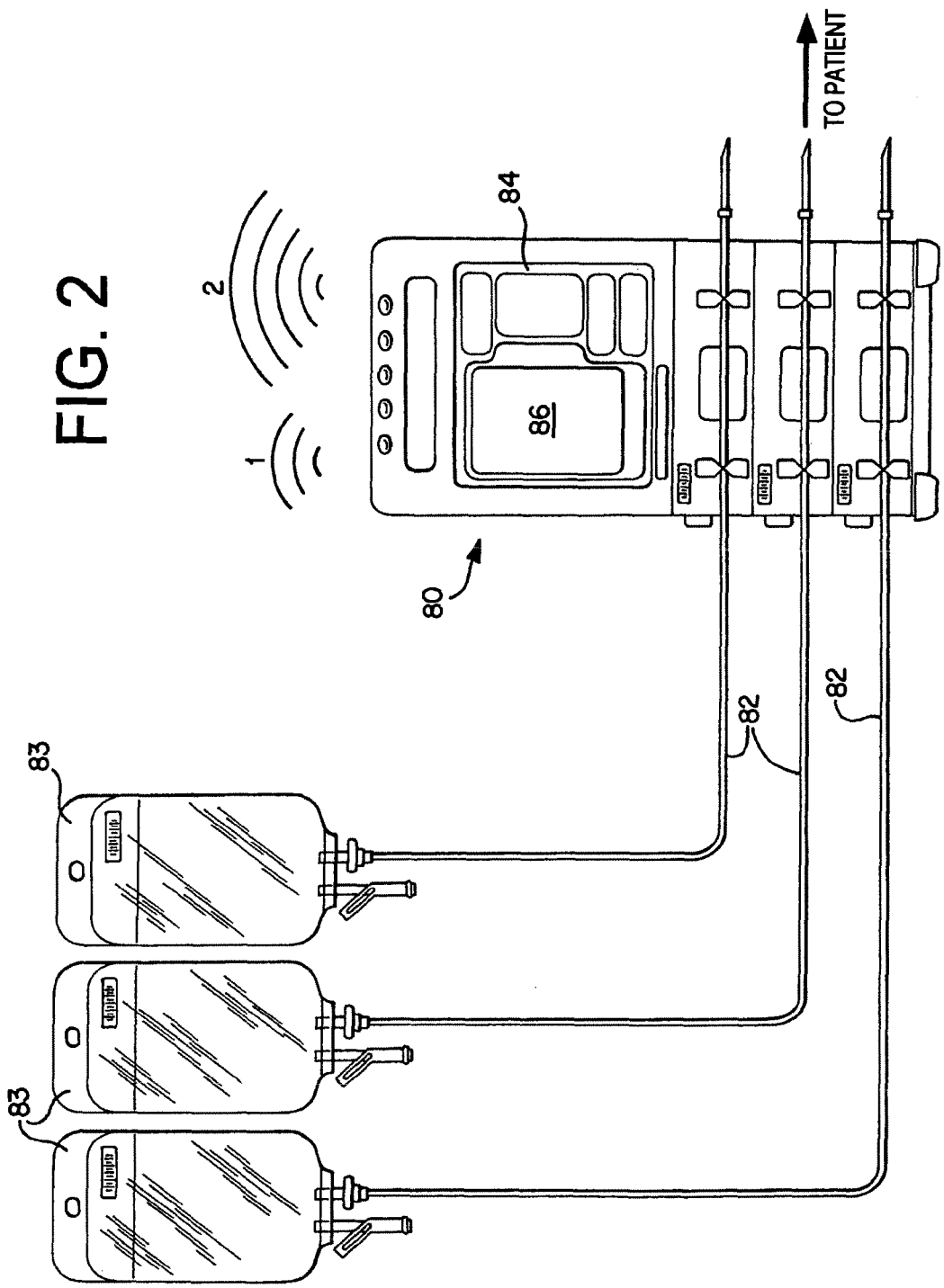
FIG. 2 is a schematic diagram depicting an infusion pump having an alarm system that includes an audible component in accordance with the principles of the present invention.

Referring to FIG. 2, a pump 80 is shown having three line sets 82 loaded therein to facilitate delivery of three fluid types to a patient. The pump 80 is preferably an infusion pump. Each of the line sets 82 is associated with a container 83 containing a fluid being delivered to the patient. The pump 80 includes a user interface 84 having a display 86 that can be utilized for displaying a visual form of the alarm 60. Although not shown, a light indicator, such as an LED or other source of light, could be incorporated into the pump and act as a visual form of the alarm 60. FIG. 2 schematically depicts a first audible alarm state (1) and a second audible alarm state (2), wherein the second alarm state is discernable from the first alarm state because it is at a higher volume level than the first alarm state. The audible alarm states can also be discernable by tone, by frequency of an interval, by type of sound, or by any other means to create a perceptively different state between the two alarm states.

Figure 3:
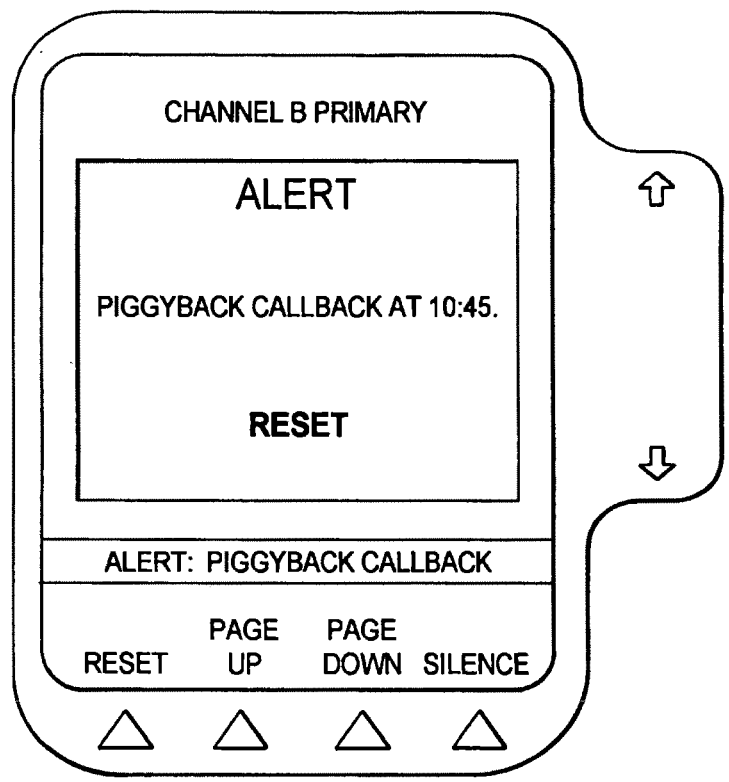
FIG. 3 is a screen shot of a display of the infusion pump depicted in FIG. 3, which illustrates an exemplary visual first alarm state of the alarm system.

As already noted, the pump 80 of FIG. 2 can also incorporate a visual form of the alarm 60. As an example of a visual form of the alarm 60, FIG. 3 depicts a screenshot of the display 86 that shows an alert that may not be of a high level of importance and is therefore categorized as a first alarm state. In this example, a caregiver enabled a callback feature relating to a piggyback function of the pump 80. Thus, when the piggyback infusion has been completed and the pump channel has switched over to the primary rate, a first alarm state is activated in the form of an alert as shown on the screenshot in FIG. 3.

Figure 4:
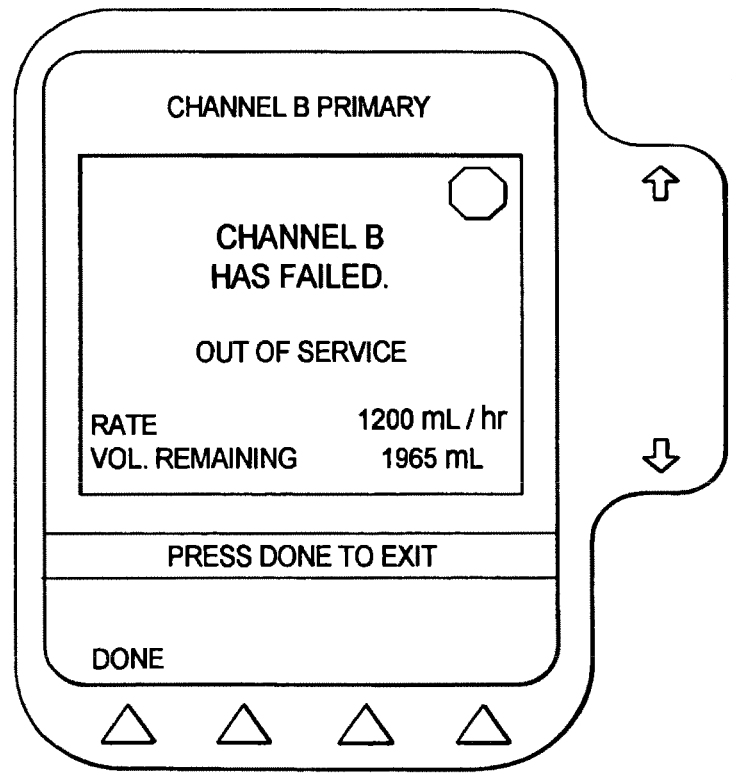
FIG. 4 is a screen shot of a display of the infusion pump depicted in FIG. 3, which illustrates an exemplary visual second alarm state of the alarm system.

As an example of a visual form of the alarm 60 in the second alarm state, FIG. 4 depicts a screenshot of the display 86 that shows an alert that may be of a high level of importance and is therefore categorized as a second alarm state. In this example, a channel of the pump 80 has failed and is out of service. Since this may be critical, a second alarm state is activated in the form shown on the screenshot in FIG. 4. It is understood that in such a case, an audible alarm may also be incorporated into the alarm state as well.

In certain instances, it may be desirable to allow a user to program certain events to be associated with a particular alarm state. Preferably such programming is done by personnel 30 authorized by a health care facility so that it can be in accordance with facility policy and procedures. In a particular embodiment, the second alarm state may be programmed to only be operational with a particular fluid, such as a particular drug. The alarm states can also be programmed to indicate drug interaction situations. In such embodiments, the identification of a particular fluid having an associated alarm, or data tables or libraries indicating potential drug interactions, can be stored in a memory associated with the pump.

Figure 5:
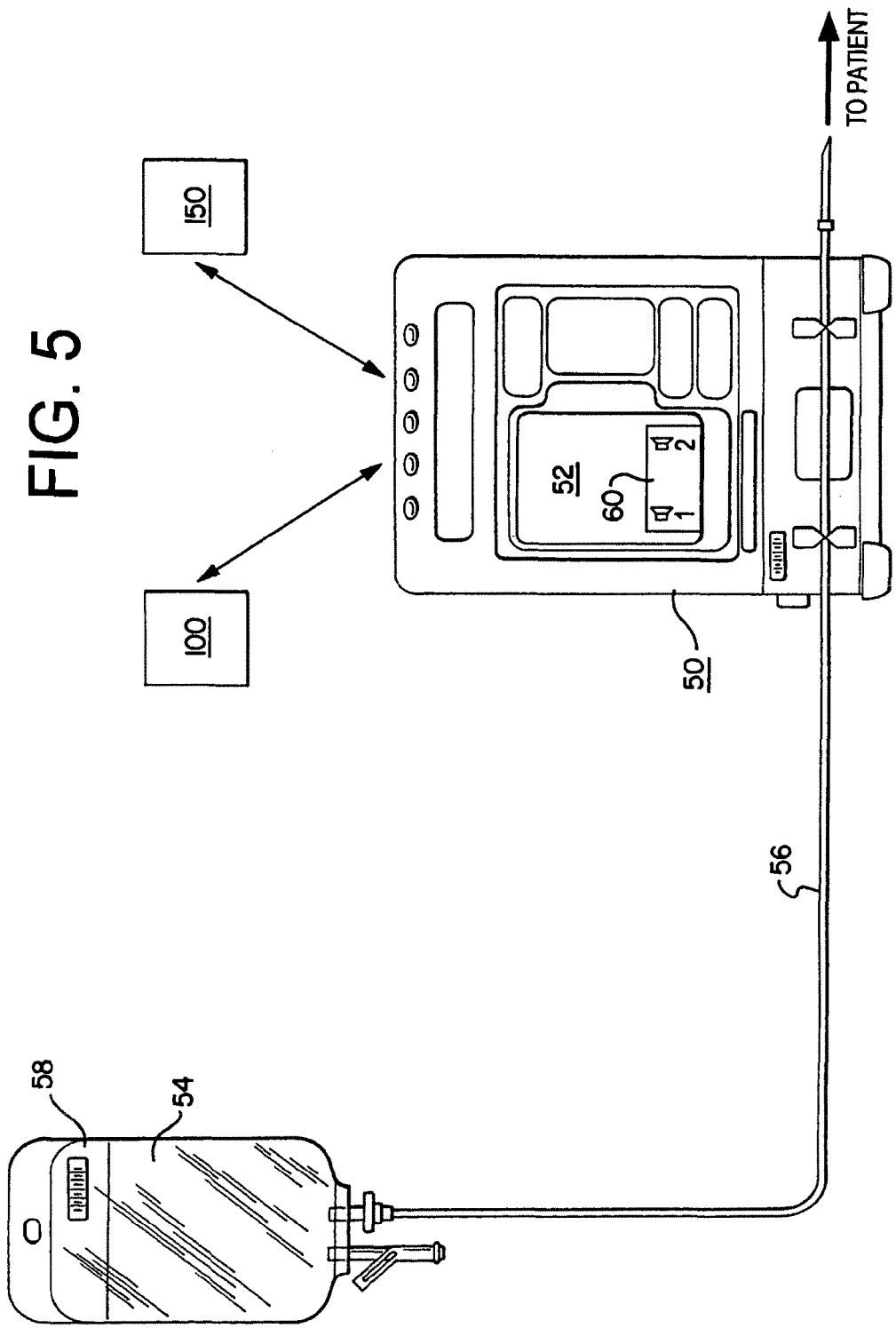
FIG. 5 is a schematic diagram generically depicting an infusion pump having an alarm system in communication with at least one external device in accordance with the principles of the present invention.

As shown in FIG. 5, according to another aspect of the invention, the alarm system 52 and associated alarm 60 can be linked to one or more external sources or devices 100, such that the alarm system 52 can be utilized by these external sources. In such a case, the external source or device 100 would be associated with the treatment parameter to be monitored. For example, a heart rate monitor or a pulse oximeter may be connected to the alarm system 52 to allow treatment parameters of these devices, and events relating to the treatment parameters of these devices, to be associated with the alarm states of the alarm system 52. In such cases, there may be several external devices or sources that utilize the alarm system 52 to provide an effective multi-state alarm.

As shown in FIG. 5, according to yet another aspect of the invention, the alarm system 52 may be in communication with an external device or system 150 to allow routing of an alarm state signal to that external device or system. For example, the external system 150 may be a centralized server or computer that could allow an alarm state and associated information, such as the associated event, treatment parameter, device, patient identification, or the like, to be routed to other devices, such as another computer, a personal digital assistant (PDA), pager, wireless e-mail device, wireless telephone or communicator, or the like. Such an arrangement expands the effectiveness of a multi-state alarm system.

It is understood that the alarm system 52 is customizable in a variety of different methods. For example, the system 52 can be set such that a first drug is associated with an alarm escalation wherein the alarm has a first state and a second state as described above. The system 52 is also set such that a second drug is not associated with an alarm escalation. The system 52 can further be set such that in non-critical alarms, the pump continues to run. However, with critical alarms, the pump is shut down.

Figure 6:
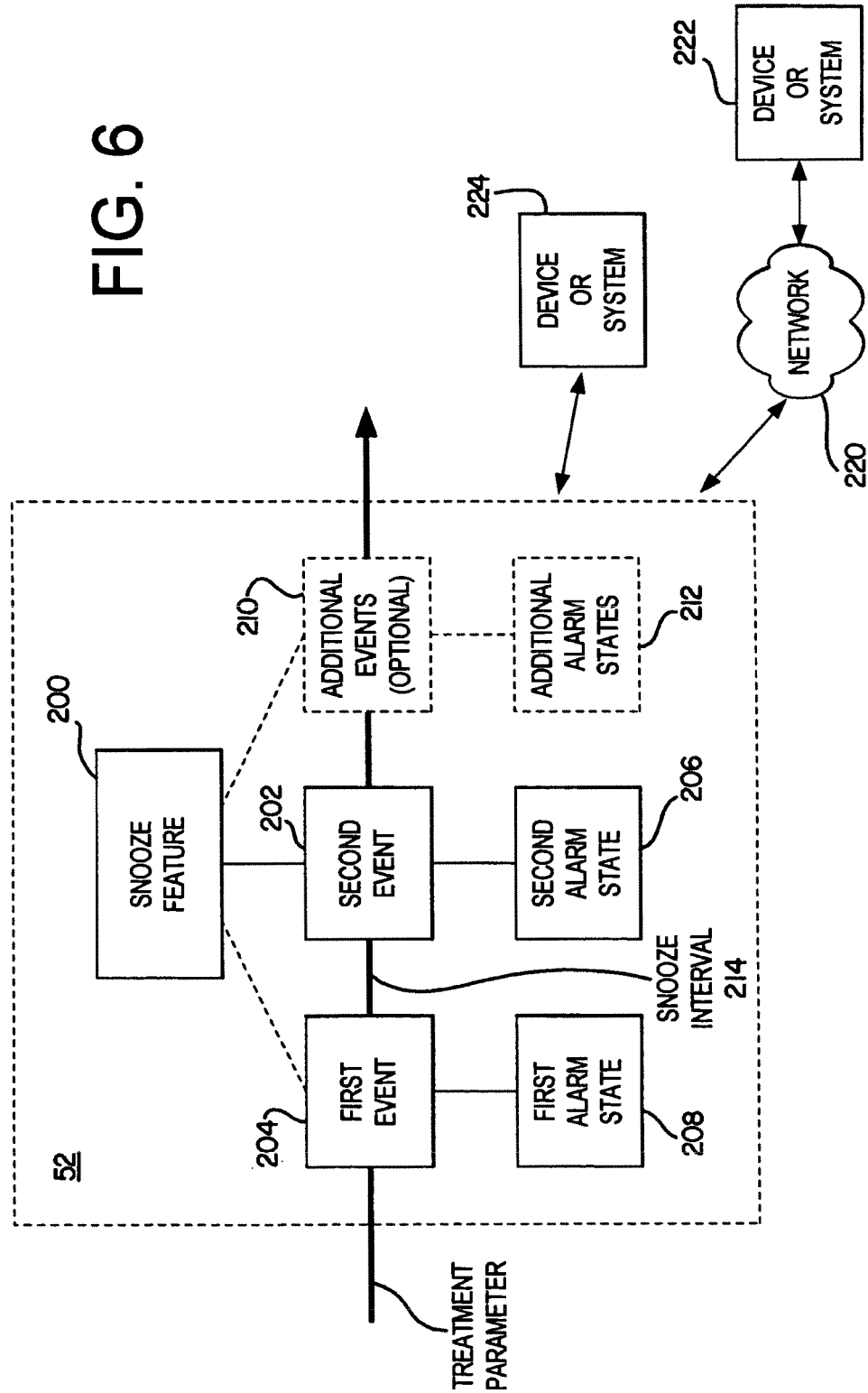
FIG. 6 is a schematic diagram of an alternate embodiment of the alarm system of the present invention incorporating a near-end alert/alarm feature or snooze feature.

FIG. 6 discloses a schematic diagram of yet another aspect of the alarm system 52 of the present invention. In this embodiment, the alarm system 52 incorporates a customizable near-end alert/alarm having a "snooze" feature 200, snooze element or delay element. This aspect allows a user to define or enable a second event 202 relative to a first event 204 or relative to when a caregiver addresses the first event 204. For example, the snooze feature 204 may define or enable the second event 202 in terms of: expiration of an amount of time relative to either the first event 204 or when a caregiver addresses the first event 204; reaching a value of a treatment parameter relative to either the first event 204 or when a caregiver addresses the first event 204; or any other type of data, information, or parameter that may change relative to either the first event 204 or when a caregiver addresses the first event 204. When the second event 202 occurs, a second alarm state 206 is activated wherein the second alarm state 206 is discernable from a first alarm state 208 associated with the first event 204. The snooze feature 200 may be configured such that additional events 210 may be thereafter defined, each associated with the second alarm state 206, or additional alarm states 212 that are all respectively discernable.

As already discussed above, in accordance with a particular embodiment, the second event 202 can be defined by an amount of time that has expired since the first alarm state 208 has been activated without being addressed by a caregiver. In a related aspect incorporating the snooze feature 200, when the caregiver addresses the first alarm state 208, the snooze feature 200 can be incorporated into the alarm system 52 to allow the caregiver to acknowledge the first event 204 and define the second event 202 in terms of a predetermined amount of time measured relative to either the first event 204 or when the caregiver addressed the first event 204, i.e. a snooze interval 214. When the snooze feature 200 is activated by the caregiver, the second alarm state 206 is enabled and the second event 202 is set by a predetermined value or preprogrammed data stored in a memory, or by data entered or obtained at the time of activation of the snooze feature 200, which represents the snooze interval 214. After expiration of the snooze interval 214, the second alarm state 206 is activated. The snooze feature 200 may be configured such that additional events 210 and associated snooze intervals may be thereafter defined by further activation of the snooze feature 200. The second alarm state 206, or one or more additional alarm states 212, may be associated with these additional events 210.

As mentioned above, in a particular embodiment, the snooze feature or snooze element 200 may define the second event 202 in terms of a predetermined value of a treatment parameter relative to the first event 204 or when a caregiver addresses the first event 204. In a specific example of this particular embodiment, the treatment parameter may be related to the volume of an infusion of a medicament, such as a fluid, to a patient. The first event 204 may be defined in terms of a predetermined volume level value or in terms of units of time remaining until a predetermined volume level value is reached during treatment of the patient by infusion. When the first event 204 occurs and the first alarm state 208 is activated, the caregiver may activate the snooze feature 200, which deactivates the first alarm state 208. In this example, activation of the snooze feature 200 will define or enable the second event 202 in terms of a second volume level value or increment, or in terms of units of time until a volume level value is reached during the treatment of the patient. When the particular value associated with the second event 202 is reached, the second alarm state 206 is activated. The snooze feature 200 may be configured such that additional events 210 may be thereafter defined by further activation of the snooze feature 200. The second alarm state 206, or one or more additional alarm states 212, may be associated with these additional events 210. When the treatment parameter is related to the volume in an infusion application, the events can act as notifications to the caregiver that a particular point in the infusion treatment has been reached. Notification before the end of an infusion, i.e. a "near-end" alert, provides the caregiver the opportunity to avoid interruption in therapy, unwanted changes in the rate of infusion, or other occurrences that may adversely affect treatment of the patient. To avoid such occurrences, the caregiver can use the time after notification and before the end of the infusion to prepare and set-up a new container or infusion kit.

In a particular embodiment, the alarm system 52 is in communication with a computer network 220 of a healthcare facility to allow communication with other devices or systems 222 within the facility. In such an embodiment, for example, a pharmacy of the facility can be automatically notified of one or more of the events so that a new container of fluid or drug can be prepared in time to avoid an interruption in the infusion therapy of the patient. The alarm system 52 can also be in direct communication, including wireless communication, with a device or system 224 to allow for various control options of the system or alarm state duplication or notification within the device or system 224. In addition, the alarm system 52 can be utilized for infusion of medicaments contained in flexible bags, syringes or semi-rigid containers. It is further understood that the alarm system 52 can occur on an infusion device such as an infusion pump shown in the Figures, but also on a handheld device, a nurse paging system or a central monitoring system.

It should be appreciated that the snooze feature 200 can be implemented in numerous applications in accordance with the principles of the present invention, and as disclosed in the configurations shown in FIGS. 1-5 and 8. For purposes of exemplification of a particular application of this feature and/or one or more other aspects of the present invention, the following example is provided and certain aspects thereof are schematically illustrated in FIG. 7. It should be understood that this example is one of many possible applications of the principles of the present invention and should in no way be construed to limit the scope of the present invention to the details of this particular example.

EXAMPLE

In this particular example, a customizable "near-end" alarm system 250 having a snooze feature 252 is provided for use in connection with an infusion pump used to deliver a medicament or fluid to a patient via infusion. The alarm system 250 is associated with the pump and can be incorporated into the pump, or a separate device or system, such as a personal digital assistant (PDA) or other portable computing device, a paging system, monitoring system, or other device, network, or system. The near-end alarm system 250 can be customizable to a specific drug infusion wherein the snooze feature 252 allows for notification to the caregiver before the end of the infusion. The notification is in the form of a first and/or a second alarm state 254 and 256 of the alarm system 250, which can be audible, visual, or both. In this example, the alarm states 254 and 256 notify the caregiver that the infusion volume remaining will soon reach a predetermined value (which is zero in this case, although other values are possible) so that the caregiver can respond to the notification, such as by hanging a new fluid container and resetting the volume to be infused via the pump. This prevents the infusion from dropping to a lower rate that could potentially adversely affect the patient's hemodynamic status.

In this example, a first event 260 is defined by the infusion volume reaching a first value or parameter X, which can be preprogrammed; programmed at the point of care for a specific drug infusion such as at the bedside; obtained via an identification or data associated with a line set or container, such as a barcode label, RFID, or the like; obtained from an external device, such as a handheld device or other external device; or obtained from an external source via a network connection; or the like. Alternatively, the first event 260 can be defined by a value or parameter representing an amount of time remaining before the end of the infusion (for example, the number of minutes remaining before the end of the infusion). The value associated with the first event 260 can be a component of a predetermined drug specific profile associated with a container of a specific drug or line set type. A second event 262 is also defined by the infusion volume reaching a second value or parameter Y, which can be programmed or obtained in similar fashion to that of the first value X. If desired, additional events defined by respective values may also be programmed.

When the first value X is reached during infusion, the first alarm state 254 is activated, thereby notifying the caregiver. The first value X could represent 30 minutes remaining before completion of the infusion. The caregiver can then activate the snooze feature. Activation of the snooze feature 252 of the alarm system 250 allows the second event 262 to be set within the system so that upon occurrence of the second event 254, i.e., the infusion volume reaching the second value Y, the second alarm state 262 is activated to further notify the caregiver. In a preferred embodiment, the second alarm state 262 is discernable from the first alarm state 260 to ensure that the caregiver will be notified of the second event 254, especially in critical applications. If additional events have been programmed, the snooze process can be continued for each of the additional events. In a particular embodiment with only two programmed events, the first alarm state 252 and/or the second alarm state 254 comprises an escalating alarm that escalates as the volume value (or time value) decreases from the second value to notify the caregiver of the rate of decreasing volume (or time). Depending on the type of alarm, the escalation could be in the form of an increase in volume, a change in the type of tone, a change in the interval or frequency of the tone, the activation of, or a change in appearance of, one or more visual indicators, or any combination thereof. This escalation process can also be incorporated in embodiments having more than two event and associated alarm states. The alarm system 52 could have a more urgent (using any of the discernable alerts described above) near-end alert/alarm for a designated high alert or in critical infusion therapies.

In a particular embodiment, the alarm system 250 is in communication with a computer network 270 of the healthcare facility to allow communication with other systems 272 within the facility. In such an embodiment, for example, a pharmacy of the facility can be automatically notified of one or more of the events so that a new container of fluid or drug can be prepared in time to avoid an interruption in the infusion therapy of the patient.

With such features of the alarm system 52, a clinician is alerted that a volume to be infused will soon be zero so the clinician can respond to the alert, set up a new container and reset the volume to be infused. This prevents an infusion from dropping to an unwanted or undesirable lower rate and also prevents an interruption of therapy. The delay or snooze feature is completely customizable wherein the alarm system 52 can be configured as desired.

FIG. 8 shows another embodiment of an alarm system of the present invention, generally designated with the reference numeral 352. The alarm system 352 is similar to the embodiments described above, however, the alarm system 352 is utilized with a disposable element or micro electromechanical system (MEMS) element. In one preferred embodiment, the MEMS element is a MEMS pump. It is understood, however, that the pump could be any type of disposable pump including pumps micro-molded in plastic or otherwise manufactured on a small scale. As shown in FIG. 6, alarm system 352 may be used in conjunction with a medication delivery system, generally designated with the reference numeral 300. The system 100 generally includes a medical device 312, preferably a MEMS pump 312, which may have an associated controller 330, an administration line set 314, a container 316. The system 100 may also take the form of any of the systems such as disclosed in commonly-owned U.S. patent application Ser. No. 10/040,887, entitled "Infusion System," which application is expressly incorporated by reference herein.

The container 316 is a container similar to the container 16 described above. In one preferred embodiment, the container 316 is a flexible bag adapted to contain a medication such as a medicament or medical fluid. The administration line set 314 is similar the line set 14 described above. The line set 314 includes a tubing having one end connected to or otherwise in communication with the container 316 and another end having a catheter or other device for communication with the patient.

As further shown in FIG. 5, the MEMS pump 312 is operably associated with the line set 314. The MEMS pump 312 may be connected to the line set 314 in various configurations. For example, the MEMS pump 312 may have an inlet port 320 and an outlet port 322 wherein the MEMS pump 312 is connected at an intermediate portion of the line set 314. Accordingly, a portion of the line set 314 is connected to the inlet port and a portion of the line set 314 is connected to the outlet port 322 wherein the MEMS pump 312 is operably connected to the line set 314. Once properly connected, the MEMS pump 312 can pump fluid from the container 316 to the patient.

As discussed, the pump 312 may be a MEMS pump 312. MEMS devices are typically etched in silicon. It is further understood that MEMS may also describe other types of micro electromechanical system devices such as devices that are micro-molded in plastic. Thus, MEMS devices may include devices etched in silicon, molded in plastic or otherwise fabricated on a small scale.

As discussed, the system 300 may further use the controller 330. The controller 330 is operably associated with the MEMS pump 312. The controller 330 may communicate with the MEMS pump 312 via a wireless connection. Alternatively, a hard connection may be utilized wherein the MEMS pump 312 may be plugged into the controller 330. While the controller 330 is shown as a separate component in one preferred embodiment, it is understood that the controller 330 may be integral with the MEMS pump 312.

Similar to the discussion above, the controller 330 incorporates the alarm system 352. The alarm system 352 operates with the controller 330 and in cooperation with the MEMS pump 312. It is further understood that the alarm system 352 could be integral with the pump 312. The alarm system 352 is customizable and may include all of the features of the alarm systems previously described. Thus, as described, the alarm system 352 may include multiple alarm states that are discernable from one another. The alarm system 352 may also include the near-end alert/alarm feature as discussed above.

It is further understood that a pump utilized in the present invention will incorporate safety software. The safety software is capable of generating basic failure alarms wherein the pump would assume a fail safe condition such as no free flow of medicament through the pump. Various software/pump configurations may be utilized. For example, all software may be located on the pump head, or all software may be located off of, or remote from the pump head. In addition, all software may be located off of the pump head with the exception of the specific safety software being located on the pump head.

It should be understood that the invention may be embodied in other specific forms without departing from the spirit or central characteristics thereof. The present embodiments, therefore, are to be considered in all respects illustrative and not restrictive, and the invention is not to be limited to the details given herein.

The invention is claimed as follows:

1. A medical fluid delivery system comprising:
   an infusion pump configured to deliver medical fluid to a patient according to at least one treatment parameter; and
   an alarm feature associated with the infusion pump, the alarm feature including
   (i) a first alarm signal caused by a first alarm state associated with a first event relating to the at least one treatment parameter,
   (ii) a second alarm signal caused by a second alarm state associated with a second event relating to the at least one treatment parameter, the second alarm signal discernable from the first alarm signal, and
   (iii) a snooze element configured to deactivate the first alarm state after the first event has occurred and to enable the second alarm state to be activated upon occurrence of the second event.

2. The medical fluid delivery system of claim 1, wherein the at least one treatment parameter is associated with the infusion pump.

3. The medical fluid delivery system of claim 1, wherein the at least one treatment parameter is associated with a source external to the infusion pump.

4. The medical fluid delivery system of claim 1, wherein the first alarm signal and the second alarm signal are provided by at least one device selected from the group consisting of: a computer; a personal digital assistant; a pager; a wireless e-mail device; or a wireless telephone or communicator.

5. The medical fluid delivery system of claim 1, which includes a user interface that allows a user to program the first alarm state and the second alarm state.

6. The medical fluid delivery system of claim 1, wherein the second alarm signal includes visual text that is different from visual text associated with the first alarm signal.

7. The medical fluid delivery system of claim 1, wherein the second alarm signal has a volume level that is discernable from a volume level of the first alarm signal.

8. The medical fluid delivery system of claim 1, wherein the second alarm signal has a tone that is discernable from a tone of the first alarm signal.

9. The medical fluid delivery system of claim 1, wherein the second alarm signal has a frequency that is discernable from a frequency of the first alarm signal.

10. The medical fluid delivery system of claim 1, wherein the second alarm signal is an escalation of a tone, volume or frequency associated with the first alarm signal.

11. The medical fluid delivery system of claim 1, wherein the second alarm signal has an appearance that is discernable from an appearance of the first alarm signal.

12. The medical fluid delivery system of claim 1, wherein the first event is defined by a deviation from a value of the at least one treatment parameter, and wherein the second event is defined by an expiration of an amount of time measured from an occurrence of the first event.

13. The medical fluid delivery system of claim 1, wherein the first event is associated with a non-life-threatening situation for the patient, and wherein the second event is associated with a life-threatening situation for the patient.

14. A medical fluid delivery system comprising:
   an infusion pump configured to deliver medical fluid to a patient according to at least one treatment parameter; and
   an alarm feature associated with the infusion pump, the alarm feature including (i) a first alarm signal caused by a first alarm state associated with an event relating to the at least one treatment parameter, and (ii) a snooze element configured to deactivate the first alarm state after the event has occurred and to enable a second alarm signal caused by a second alarm state to be activated when a predefined amount of time has expired from the occurrence of the event, the second alarm signal discernable from the first alarm signal.

15. The medical fluid delivery system of claim 14, wherein the predefined amount of time is set according to (i) a predetermined value or (ii) preprogrammed data stored in a memory.

16. The medical fluid delivery system of claim 14, wherein the predefined amount of time is entered or obtained at a time of activation of the snooze feature.

17. The medical fluid delivery system of claim 14, wherein the event is based on an amount of time remaining until a predetermined volume of the medical fluid is delivered to the patient.

18. The medical fluid delivery system of claim 14, wherein the event is based on an amount of time remaining until an end of delivery of the medical fluid to the patient.

19. A medical fluid delivery system comprising:
   an infusion pump configured to deliver medical fluid to a patient according to at least one treatment parameter; and
   an alarm feature associated with the infusion pump, the alarm feature including
   (i) a first alarm signal caused by a first alarm state associated with a first deviation from an original value of the at least one treatment parameter,
   (ii) a second alarm signal caused by a second alarm state associated with a second deviation from the original value of the at least one treatment parameter, the second alarm signal discernable from the first alarm signal, and
   (iii) a snooze element configured to deactivate the first alarm state after the first deviation has occurred and to enable the second alarm state to be activated upon occurrence of the second deviation.

20. The medical fluid delivery system of claim 19, wherein the first deviation is a non-critical deviation from the original value of the at least one treatment parameter, and the second deviation is a critical deviation from the original value of the at least one treatment parameter.

21. The medical fluid delivery system of claim 19, wherein the infusion pump continues to run after the first alarm state is activated and shuts down after the second alarm state is activated.

22. The medical fluid delivery system of claim 19, wherein the at least one treatment parameter is associated with at least one of: (i) administration of the medical fluid to the patient; (ii) a measurement from the patient; and (iii) an operation of the infusion pump.

23. The medical fluid delivery system of claim 1, wherein the first alarm signal causes a visual or audible alarm associated with the first alarm state, and the second alarm signal causes a visual or audible alarm associated with the second alarm state.

24. The medical fluid delivery system of claim 14, wherein the first alarm signal causes a visual or audible alarm associated with the first alarm state, and the second alarm signal causes a visual or audible alarm associated with the second alarm state.

25. The medical fluid delivery system of claim 19, wherein the first alarm signal causes a visual or audible alarm associated with the first alarm state, and the second alarm signal causes a visual or audible alarm associated with the second alarm state.

* * * * *